(12) United States Patent
Cogan et al.

(10) Patent No.: US 10,603,502 B2
(45) Date of Patent: Mar. 31, 2020

(54) IMPLANTABLE WIRELESS MICROSTIMULATOR FOR PERIPHERAL NERVES

(71) Applicants: The Charles Stark Draper Laboratory, Inc., Cambridge, MA (US); Board of Regents, The University of Texas System, Austin, TX (US)

(72) Inventors: Stuart Cogan, Dallas, TX (US); Daniel Kenneth Freeman, Reading, MA (US); Jonathan Michael O'Brien, Tampa, FL (US); Mario Romero-Ortega, Coppell, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 74 days.

(21) Appl. No.: 15/724,490

(22) Filed: Oct. 4, 2017

(65) Prior Publication Data

US 2018/0093099 A1    Apr. 5, 2018

Related U.S. Application Data

(60) Provisional application No. 62/404,100, filed on Oct. 4, 2016.

(51) Int. Cl.
| | | |
|---|---|---|
| *A61N 1/37* | (2006.01) | |
| *A61N 1/378* | (2006.01) | |
| *A61N 1/372* | (2006.01) | |
| *A61N 1/36* | (2006.01) | |
| *A61N 1/05* | (2006.01) | |

(52) U.S. Cl.
CPC ......... *A61N 1/3787* (2013.01); *A61N 1/3605* (2013.01); *A61N 1/36125* (2013.01);
(Continued)

(58) Field of Classification Search
CPC ................ A61N 1/3787; A61N 1/0556; A61N 1/37217; A61N 1/37205; A61N 1/3605
See application file for complete search history.

(56) References Cited

U.S. PATENT DOCUMENTS 6,735,474 B1    5/2004    Loeb et al.
6,836,684 B1    12/2004   Rijkhoff et al.
(Continued)

FOREIGN PATENT DOCUMENTS

WO    2017136270 A1    8/2017

OTHER PUBLICATIONS

ISR/WO corresponding to International Application No. PCT/US17/55024, dated Dec. 28, 2017, 13 pages.

*Primary Examiner* — Allen Porter
*Assistant Examiner* — Natasha Patel
(74) *Attorney, Agent, or Firm* — Christopher S. Dodson; Nexsen Pruet, PLLC

(57) ABSTRACT

In one aspect, implantable wireless microstimulators are described herein. In some embodiments, a microstimulator described herein includes an energy harvesting circuit configured to receive an input signal and generate an electrical signal based on the received input signal. The microstimulator further comprises a diode rectifier in series with the energy harvesting circuit. The diode rectifier is configured to rectify the electrical signal. The energy harvesting circuit and the diode rectifier can be encapsulated within a biocompatible electrically insulating material. Additionally, in some cases, an electrical interface is exposed through the biocompatible electrically insulating material. A microstimulator described herein can also include a nerve cuff. The nerve cuff can be configured to receive a monophasic neural stimulation pulse through the electrical interface of the micro stimulator. Moreover, the nerve cuff can be placed
(Continued)

around a targeted peripheral nerve to provide a monophasic stimulation pulse to the peripheral nerve.

22 Claims, 9 Drawing Sheets

(52) U.S. Cl.
CPC ........ *A61N 1/37205* (2013.01); *A61N 1/0556* (2013.01); *A61N 1/37217* (2013.01)

(56) References Cited

U.S. PATENT DOCUMENTS

| | | | |
|---|---|---|---|
| 7,047,078 | B2 | 5/2006 | Boggs, II et al. |
| 8,494,643 | B2 | 7/2013 | Cowan et al. |
| 2005/0154426 | A1 | 7/2005 | Boveja et al. |
| 2007/0282378 | A1* | 12/2007 | Huang ................. A61N 1/3787 607/2 |
| 2012/0283800 | A1 | 11/2012 | Perryman et al. |
| 2013/0006039 | A1 | 1/2013 | Sadler |
| 2013/0197609 | A1 | 8/2013 | Moore et al. |
| 2014/0357933 | A1* | 12/2014 | Lee .......................... A61N 2/02 600/12 |
| 2015/0127068 | A1 | 5/2015 | Simon et al. |
| 2015/0196590 | A1* | 7/2015 | Sampson ............... A61K 33/20 424/445 |
| 2015/0297900 | A1 | 10/2015 | Perryman et al. |
| 2016/0038745 | A1 | 2/2016 | Faltys et al. |
| 2017/0209705 | A1* | 7/2017 | Faltys ................. A61N 1/3787 |
| 2017/0216606 | A1 | 8/2017 | Bernstein et al. |
| 2017/0216607 | A1 | 8/2017 | Bernstein et al. |

\* cited by examiner

IMPLANTABLE WIRELESS MICROSTIMULATOR FOR PERIPHERAL NERVES

CROSS REFERENCE TO RELATED APPLICATIONS

This application claims priority pursuant to 35 U.S.C. § 119(e) to U.S. Provisional Patent Application Ser. No. 62/404,100, filed on Oct. 4, 2016, which is hereby incorporated by reference in its entirety.

BACKGROUND

Electrical nodes can be implanted into the body of a patient for the purpose of stimulating nervous tissue. Typically, such devices include wired electrodes that receive energy from a source located outside the body. Implantable devices that connect to an external power source with wires are very invasive, and can cause long term damage to neural tissue. Wireless neural implants are available, but existing ones that are small are unable to provide neural stimulation pulses of sufficient voltage and current to effectively stimulate nervous tissue. Additionally, wireless neural implants with active components such as transistors or microcontrollers can be invasive with increased risks and discomfort to a patient. Also, including active components requires a larger receiving antenna which results in more tissue damage. Therefore, improved implantable devices for neural stimulation are needed.

SUMMARY

Microstimulators, nerve stimulation systems, and corresponding methods of stimulating nerves are described herein. For example, in one aspect, an implantable wireless microstimulator is described herein, wherein the microstimulator has no active components, such as transistors or microcontrollers. The absence of such active components can permit the microstimulator to have a small total volume or to be implemented in a package with a small total volume (such as a volume of less than 1 cubic millimeter or less than 0.5 cubic millimeters). In some embodiments, an implantable wireless microstimulator described herein includes or comprises an energy harvesting circuit that receives or is configured to (1) receive an input signal and (2) generate an electrical signal based on the received input signal. The microstimulator further comprises a diode rectifier. More particularly, the diode rectifier can be in series with the energy harvesting circuit. Moreover, the diode rectifier rectifies or can be configured to rectify the electrical signal generated by the energy harvesting circuit. Additionally, in some cases, the energy harvesting circuit and the diode rectifier are both encapsulated within a biocompatible electrically insulating material. The encapsulated combination of energy harvesting circuit and diode rectifier can have a small volume. For example, in some instances, the encapsulated combination of energy harvesting circuit and diode rectifier is less than about 1 cubic millimeter or less than about 0.5 cubic millimeters.

A wireless microstimulator described herein, in some instances, also includes one or more electrical interfaces. Such an interface, in some embodiments, is exposed or accessible through the biocompatible electrically insulating material.

A microstimulator described herein can further include or be attached to a nerve cuff. The nerve cuff, in some cases, receives or is configured to receive a monophasic neural stimulation pulse through the electrical interface of the micro stimulator, where the monophasic neural stimulation pulse is understood to be provided by the energy harvesting circuit and rectifier of the microstimulator. Further, the nerve cuff can be placed around a targeted peripheral nerve to provide the monophasic stimulation pulse to the peripheral nerve. The microstimulator may provide a stimulation pulse of at least 0.3V and 10 uA, providing a power of at least 3 uW. The microstimulator does not include any transistors.

Turning again to the energy harvesting circuit of a microstimulator described herein, in some implementations, the energy harvesting circuit comprises an inductor in parallel with a capacitor. In some cases, the inductor has an inductance in the range of about 10 nH to about 500 µH. Moreover, in some embodiments, the inductor includes a coil made or formed from at least one of copper, aluminum, silver or gold wound around a ferrite core. In some embodiments the coil has a wire diameter between 0.009 and 0.026 millimeters and has between 10 and 500 turns. A ferrite core, in some cases, is formed from an iron spinel of formula $MOFe_2O_3$, where M is a metal. The metal M may be Fe or a metal differing from Fe. Other spinels or ferrites may also be used. In some cases, the coil is wound within the biocompatible electrically insulating material, and the biocompatible electrically insulating material is free or substantially free from air bubbles. Substantially free from air bubbles means that no air bubbles are observable with the human eye. In some implementations, the biocompatible electrically insulating material is formed from Parylene, silicone, polyurethane, Teflon, epoxy, or a combination thereof. Further, in some instances, the inductor has a diameter that is no greater than about 0.4 millimeters and a length that is no greater than about 1 millimeter. Additionally, in some implementations, the capacitor has a capacitance in the range of about 1 pF to about 10 nF. Further, in some embodiments, the capacitor and the inductor form a circuit having a resonance frequency in the range of about 100 kHz to about 100 MHz. Moreover, in some implementations, at least two of the capacitor, the inductor, and the diode rectifier are included on a single chip. In some cases, the energy harvesting circuit can include at least one piezoelectric energy harvester.

In addition, in some implementations, a microstimulator described herein further comprises a charge storage element that stores or is configured to store a voltage from an output of the diode rectifier. A microstimulator described herein may also comprise a first switch that discharges or is configured to discharge the stored voltage to the electrical interface when the switch is in a closed position. Moreover, in some implementations, the first switch can include at least one of a microelectromechanical systems (MEMS) magnetic reed switch or an electrostatically actuated MEMS switch. In some cases, the first switch is a normally open switch configured to close in response to a wireless actuation signal. In some implementations, the first switch exhibits hysteresis, such that an amplitude of the wireless actuation signal required to close the switch is greater than an amplitude of the wireless actuation signal required to hold the switch in a closed position. Additionally, in some instances, the wireless actuation signal comprises or includes a DC component selected to be of sufficient magnitude to hold the switch in a closed position and an AC component having a frequency that matches a resonant frequency of the switch. In such cases, the sum of the amplitudes of the DC component and the AC component can be sufficient to close the switch.

Further, in some implementations, a microstimulator described herein also comprises or includes an antenna coupled to the energy harvesting circuit. In some cases, the antenna receives or is configured to receive the input signal from a transmitter and provide the input signal to the energy harvesting circuit.

Moreover, in some implementations, the electrodes of a microstimulator described herein comprise an anode and a cathode. In some cases, the anode comprises, consists essentially of, or is formed from platinum, titanium nitride, or an alloy of platinum and iridium. The anode may be coated with iridium oxide. The cathode, in some instances, comprises, consists essentially of, or is formed from platinum, titanium nitride, stainless steel, tantalum, or an alloy of platinum and iridium. Additionally, the cathode may be coated with iridium oxide.

In some implementations, n microstimulators described herein can be implanted in a single patient. Each of the microstimulators can comprise a switch, including a switch described hereinabove. Each of the n microstimulators can comprise an electrical interface wherein each of the n electrical interfaces can be connected to one of more nerve cuffs. Each of the n switches can be configured to close in response to a wireless actuation signal wherein the wireless actuation signal can be the same for all switches, different for all switches, or the same for any combination of switches. In some implementations, a nerve cuff can be connected to the electrical interface of a first implantable wireless microstimulator and can also be connected to the electrical interface of a second implantable wireless microstimulator, each of which can be individually activated, such that the polarity of the monophasic neural stimulation pulse is reversed when received from the second implantable wireless microstimulator as compared to when received from the first implantable wireless microstimulator.

In another aspect, implantable micro stimulation systems are described herein. In some embodiments, such a system comprises a plurality of implantable wireless microstimulators described herein. For instance, in some cases, the plurality of implantable wireless microstimulators individually comprise an energy harvesting circuit configured to receive an input signal and generate an electrical signal based on the received input signal; and a diode rectifier in series with the energy harvesting circuit, the diode rectifier configured to rectify the electrical signal, wherein the energy harvesting circuit and the diode rectifier are encapsulated within a biocompatible electrically insulating material. The microstimulators can further individually comprise an electrical interface exposed through the biocompatible electrically insulating material, and/or one or more nerve cuffs configured to receive monophasic stimulation pulses through one or more of the electrical interfaces of the plurality of implantable wireless microstimulators. Moreover, as described further herein, the microstimulators do not include any transistors or other active components, in some instances. Further, in some implementations, one of the nerve cuffs of the system is connected to the electrical interface of a first implantable wireless microstimulator and is also connected to the electrical interface of a second implantable wireless microstimulator, each of which can be individually activated, such that the polarity of the monophasic neural stimulation pulse is reversed when received from the second implantable wireless microstimulator as compared to when received from the first implantable wireless microstimulator.

In still another aspect, methods of stimulating a nerve are described herein. In some embodiments, such a method comprises implanting a wireless microstimulator described herein (or a plurality of microstimulators described herein) in a patient. Additionally, in some cases, at least one implanted microstimulator further comprises electrodes, and the method further comprises placing the nerve cuff around a targeted peripheral nerve so that the electrodes are in direct contact with the nerve. Such a method may also comprise receiving an input signal with the energy harvesting circuit of the microstimulator, converting the input signal into an electrical signal, rectifying the electrical signal to provide a rectified signal, and providing a monophasic neural stimulation pulse, corresponding to the rectified signal, from the wireless microstimulator to the nerve through the electrodes.

These and other embodiments are described in greater detail in the detailed description which follows.

BRIEF DESCRIPTION OF THE FIGURES

The invention and the following detailed description of certain embodiments thereof may be understood by reference to the following figures. Like reference numbers and designations in the various drawings generally indicate like elements.

DETAILED DESCRIPTION

Embodiments described herein can be understood more readily by reference to the following detailed description and examples. Elements, apparatus and methods described herein, however, are not limited to the specific embodiments presented in the detailed description and examples. It should be recognized that these embodiments are merely illustrative of the principles of the present disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10.

Similarly, when the phrase "up to" is used in connection with an amount or quantity, it is to be understood that at least a detectable amount or quantity is present. For instance, an amount or quantity "up to 10" should generally be considered to include at least a detectable non-zero amount or quantity.

Figure 1A:
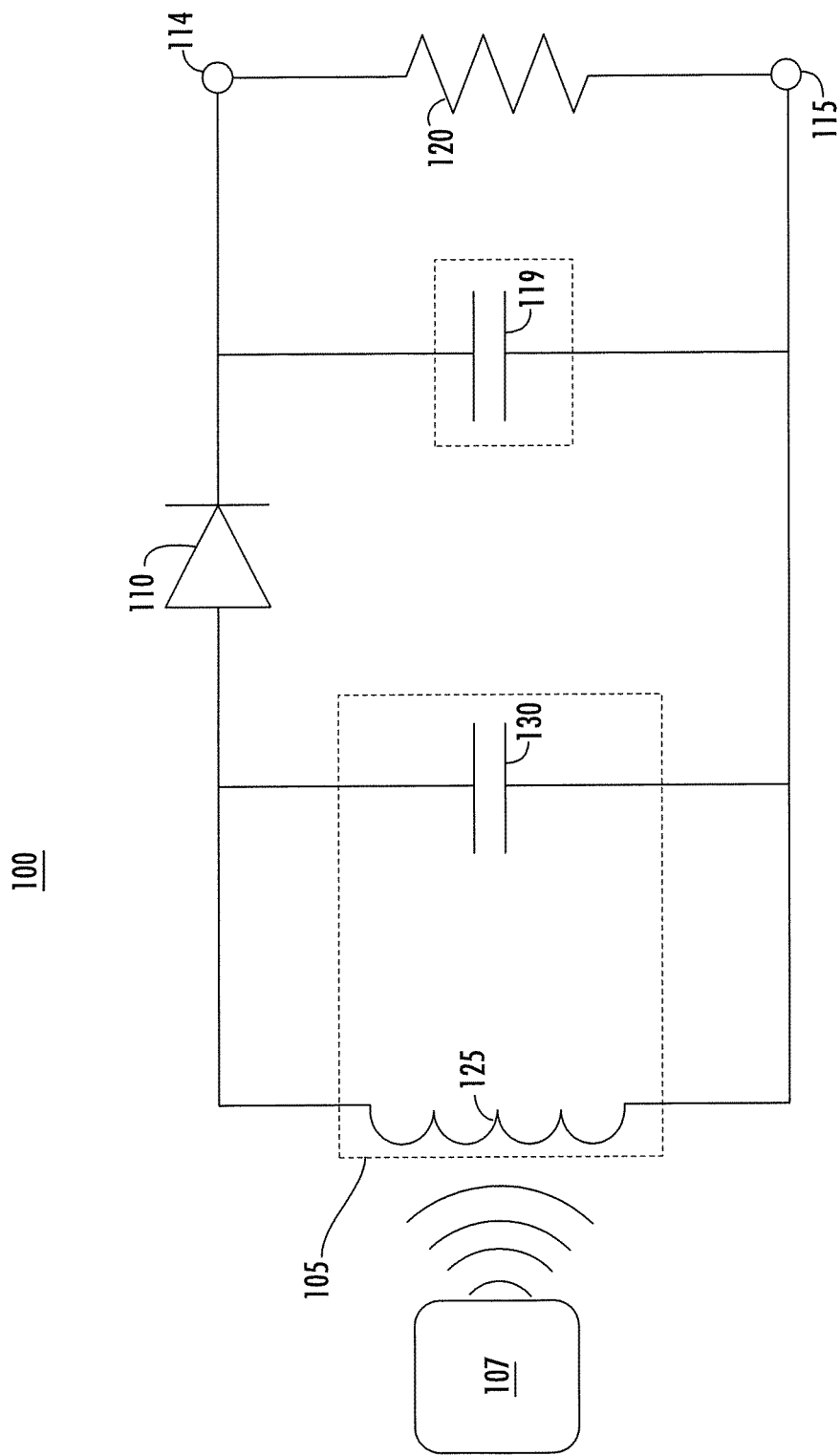
FIG. 1A shows a schematic diagram of an example implantable wireless microstimulator, according to an illustrative implementation described herein.

FIG. 1A shows a schematic diagram of an example implantable wireless microstimulator 100, according to an illustrative implementation. The microstimulator 100 includes an energy harvesting circuit 105 in series with a diode rectifier 110. Nervous tissue 120 is modeled as a resistor. Electrodes 114 and 115 receive an electrical signal from the energy harvesting circuit 105 and diode rectifier 110 through an electrical interface, and deliver a monophasic neural stimulation pulse to the nervous tissue 120, which may include a muscle, a nerve or a bundle of nerves targeted for stimulation. The electrodes 114 and 115 may be implemented in a nerve cuff. The microstimulator 100 also may include a capacitor 119. The broken line surrounding the capacitor 119 indicates that the capacitor 119 is an optional component. A power signal generator 107 is configured to deliver an input signal to the energy harvesting circuit 105. The power signal generator 107 may be external to the body of the patient. For example, the power signal generator 107 may be model AG 1012 Amplifier/Generator from T&C Power Conversion.

In the microstimulator 100 shown in FIG. 1A, the energy harvesting circuit 105 is implemented as an inductor 125 in parallel with a capacitor 130. Together, the inductor 125 and the capacitor 130 can be configured to receive the signal from the power signal generator 107, and convert the received signal into an electrical signal. For example, in some implementations the power signal generator 107 can be configured to generate an input signal in the form of an applied magnetic field. The magnetic field generated by the power signal generator 107 can be selected to ensure that it can be efficiently transmitted through the body tissue of the patient to the energy harvesting circuit 105. In some implementations, the magnetic field generated by the power signal generator can have a frequency in the range of about 100 kHz to about 100 MHz. The magnetic field induces a variable voltage across the inductor 125, which resonates with the capacitor 130. Thus, the inductor 125 and the capacitor 130, which together form the energy harvesting circuit 105, generate an electrical signal in response to the signal received from the power signal generator 107.

In some implementations, the electrical characteristics of the inductor 125 and the capacitor 130 can be selected to provide electrical resonance at a frequency matching the frequency of the magnetic field generated by the power signal generator 107. In some implementations, the capacitor 130 may be a commercially available capacitor. The capacitor 130 can have a capacitance in the range of about 1 pF to about 10 nF. The inductor 125 can have an inductance in the range of about 10 nH to about 500 µH. In some implementations, the inductor 125 can be made from a coil of conductive material, such as copper, silver, aluminum, gold, or platinum. The coil can be wound around a ferrite core within a biocompatible hermetic insulating material, such as Parylene, silicone, polyurethane, Teflon, epoxy, or a combination thereof. In some implementations, the coil has a wire diameter between 0.009 and 0.026 millimeters and has between 10 and 500 turns. A biocompatible material, in some embodiments, is non-toxic and does not cause substantial tissue inflammation. For example, an insulating material in liquid form, such as liquid silicone, can be dripped onto the inductor as the conductive coil is wrapped around the ferrite core. After the coil has been wound, the liquid insulating material can be cured. This process can help to reduce the likelihood of developing air bubbles within the insulating material. In some implementations, the ferrite core may have a diameter in the range of about 0.1 millimeters to about 0.3 millimeters. In some implementations, the inductor can have a diameter of greater than about 0.1 millimeters and less than about 0.6 millimeters. In some implementations, the inductor can have a diameter of less than about 0.5 millimeters, less than about 0.4 millimeters, less than about 0.3 millimeters, or less than about 0.2 millimeters. In some implementations, the inductor can have a length of greater than about 0.1 millimeters and less than about 1.2 millimeters. In some implementations, the inductor can have a length less than about 1.1 millimeters, less than about 1 millimeter, less than about 0.9 millimeters, or less than about 0.8 millimeters.

Because the microstimulator 100 is implanted into a patient, smaller sizes for individual components may be preferable in order to minimize health risks and discomfort to the patient. For example, in some implementations, the entire implantable microstimulator 100 can have a volume of less than about 1 cubic millimeter, less than about 0.5 cubic millimeters, less than about 0.4 cubic millimeters, less than about 0.3 cubic millimeters, or less than about 0.2 cubic millimeters. In some implementations, the microstimulator 100 may have a diameter of less than about 0.5 millimeters and a length of less than about 1.5 millimeters. In some other implementations, the microstimulator 100 may have another shape, such as a cube or a rectangular prism. In still other implementations, the microstimulator 100 may have an irregular shape.

It should be noted that, while FIG. 1A depicts the energy harvesting circuit 105 as an inductor 125 in parallel with a capacitor 130, the energy harvesting circuit 105 may also be implemented in other ways. For example, the energy harvesting circuit 105 can include a piezoelectric energy harvester. In general, piezoelectricity is electrical charge that accumulates in a material in response to mechanical stress. Thus, a piezoelectric energy harvester can be configured to respond to a signal generated by the power signal generator 107 in a way that induces mechanical stress in the piezoelectric energy harvester, which in turn causes the piezoelectric energy harvester to generate an electrical charge. In some implementations, the energy harvesting circuit 105 can be implemented as a block of lead zirconate titanate (PZT), a piezoelectric microshell transducer, a piezoelectric bimorph, a piezoelectric monomorph, or any other type of piezoelectric energy harvesting device capable of generating an electrical signal in response to an input signal received from the power signal generator 107. In such implementations, the power signal generator 107 can be configured to produce an input signal that induces mechanical stress in the piezoelectric energy harvester. For example, the piezoelectric energy harvester can be or can include an ultrasonic transducer, and the power signal generator 107 can generate an input signal that is an acoustic signal to be received by the piezoelectric energy harvester. The acoustic signal can induce stress in the piezoelectric energy harvester, which can then be converted into an electrical signal.

Other types of energy harvesting devices also may be used as the energy harvesting circuit 105. For example, the energy harvesting circuit 105 can be or can include a photovoltaic energy harvester, a pyroelectric energy harvester, a thermoelectric energy harvester, or an electrostatic energy harvester.

Furthermore, the input signal generated by the power signal generator 107 can be selected based in part on the characteristics of the components used to form the energy harvesting circuit 105. In some implementations, the signal generated by the power signal generator may include a near-field signal. In some other implementations, the signal generated by the power signal generator may include a far-field signal. In some implementations, the micro stimulator 100 may include an antenna coupled to the energy harvesting circuit. The antenna can be configured to receive the signal from the power signal generator 107 and deliver the signal to the energy harvesting circuit 105.

As discussed above, the energy harvesting circuit 105 can be configured to convert a time-varying input signal from the power signal generator 107 into a time-varying electrical signal. In some implementations, the frequencies that are most efficient for transmitting the input signal to the microstimulator 100 through the body of a patient may be significantly higher than the frequencies of neural stimulation pulses that most efficiently excite the nervous tissue 120. As a result, the frequency of the electrical signal generated by the energy harvesting circuit 105 may be too high to efficiently stimulate nervous tissue 120, because the frequency of the electrical signal produced by the energy harvesting circuit 105 will be approximately equal to the frequency of the signal received from the power signal generator 107. To address this problem, the diode rectifier 110 is positioned in series with the energy harvesting circuit 105. The diode rectifier 110 receives the electrical signal from the energy harvesting circuit 105 and produces a rectified signal having a lower frequency (i.e., a low frequency moving average voltage proportional to the amplitude of the RF electrical signal received from the energy harvesting circuit 105). This lower frequency rectified signal is then delivered to the nervous tissue 120 via the electrodes 114 and 115.

In some implementations, the electrical signal produced by the energy harvesting circuit 105 can have a relatively small magnitude. Therefore, the diode rectifier 110 may be selected to have a relatively low turn-on voltage and a low parasitic capacitance in order to efficiently convert the electrical signal from the energy harvesting circuit 105 to a rectified signal. For example, in some implementations the diode rectifier 110 may have a turn-on voltage of less than about 0.3 volts, less than about 0.2 volts, less than 0.1 volts, or less than about 0.05 volts. Examples of devices that may be suitable for use as the diode rectifier 110 can include an RF Schottky diode or an RF detector diode. In some implementations, including the optional capacitor 119 in the microstimulator 100 can help to turn on the diode at lower voltages. In some implementations, the capacitor 119 may have a capacitance in the range of about 100 pF to about 10 nF.

In some implementations, the electrodes 114 and 115 may be exposed to the nervous tissue 120 through an encapsulating layer that surrounds the other components of the implantable microstimulator 100. In these implementations, the encapsulating layer substantially encloses and seals the other components of implantable microstimulator 100 allowing only the electrodes 114 and 115 to be exposed through it. For example, the energy harvesting circuit 105 and the diode rectifier 110 can be encapsulated in a biocompatible material, such as Parylene, silicone, polyurethane, Teflon, epoxy, or a combination thereof. The electrodes 114 and 115 can be electrically connected to the energy harvesting circuit 105 and the diode rectifier 110 as shown in the schematic of FIG. 1A, but may be exposed through biocompatible encapsulation material to facilitate delivery of the neural stimulation pulse to the nervous tissue 120. The electrodes 114 and 115 can be formed from any non-toxic conductive material. In some implementations, the electrodes 114 and 115 may be formed from porous platinum. Alloy of platinum and iridium (PtIr-alloy) can also be used for electrodes 114 and 115. Other electrode materials that may be applied to the platinum or PtIr-alloy electrodes to improve charge delivery include: iridium oxide formed by sputtering, electrodeposition or thermal oxidation of iridium containing solutions, and titanium nitride deposited by sputtering. The use of iridium oxide as a coating on one or both of the electrodes may usefully increase charge delivery capabilities. Similarly, the use of titanium nitride as a coating on one or both of the electrodes may usefully increase charge delivery capabilities.

One feature of microstimulator 100 in some implementations such as when one microstimulator provides a monophasic neural stimulation pulse to a targeted peripheral nerve, is that one of electrodes 114 and 115 is always a cathode and the other electrode is always an anode, allowing for different materials or coatings. In some implementations particularly useful for increasing the capability of microstimulator 100 to provide chronic charge delivery, the cathode comprises either platinum, PtIr-alloy, or titanium nitride and the anode is coated with iridium oxide. This advantage derives from the stability of iridium oxide as an anode and the stability of platinum, PtIr-alloy or titanium nitride as a cathode. In any of the implementations employing iridium oxide or titanium nitride coatings, the underlying electrode material may be one of platinum, PtIr-alloy, titanium, stainless steel, or tantalum.

Figure 1B:
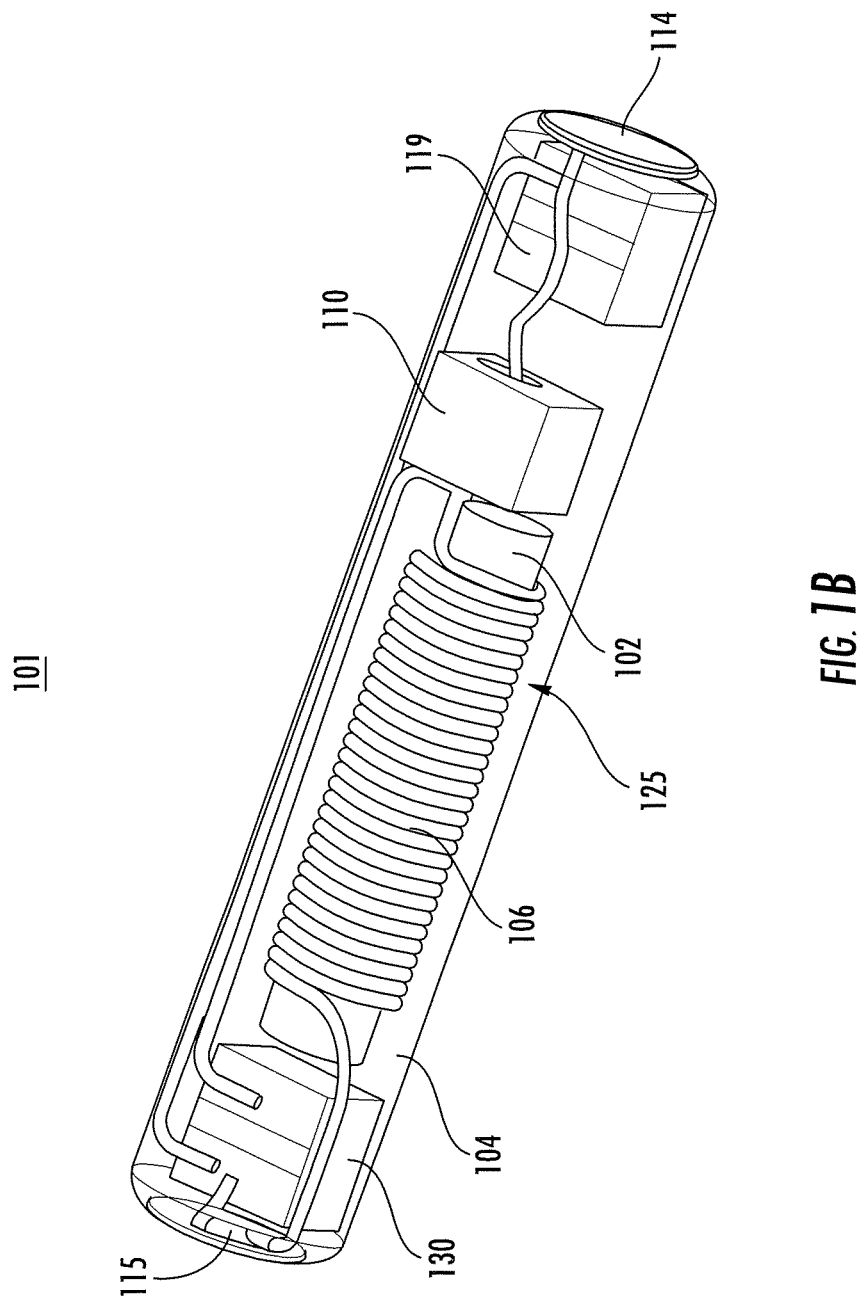
FIG. 1B shows a perspective view of an implantable wireless microstimulator including the components shown in the schematic diagram of FIG. 1A, according to an illustrative implementation described herein.

FIG. 1B shows a perspective view of an example implantable wireless microstimulator 101 including the components shown in the schematic diagram of FIG. 1A, according to an illustrative implementation. For example, the microstimulator 101 includes the inductor 125 and the capacitor 130, which together form the energy harvesting circuit 105. The inductor 125 is formed from a conductive coil 106 that is wrapped around a magnetic core 102, such as ferrite. The output of the energy harvesting circuit is electrically coupled to the rectification diode 110. The shunt capacitor 119 couples to the output of the rectification diode 110, and has a first terminal coupled to the electrode 114 and a second terminal coupled to the electrode 115.

The components of the microstimulator 101 are packaged in a manner that can allow the microstimulator 101 to have a relatively small total volume. In this example, the microstimulator 101 has a substantially cylindrical shape. Each of the components of the microstimulator 101 is included within a substantially cylindrical housing and arranged substantially along an axis of the substantially cylindrical housing. In some implementations, the microstimulator 101 may have a diameter in the range of about 0.3 millimeters to about 0.7 millimeters and a length in the range of about 1.3 millimeters to about 1.7 millimeters. Each of the capacitors 119 and 130 may have a length in the range of about 200 microns to about 300 microns, a width in the range of about 100 microns to about 150 microns, and a thickness in the range of about 100 microns to about 150 microns. For example, each of the capacitors 119 and 130 may be implemented using a capacitor having a length of 250 microns, a width of 125 microns, and a thickness of 125 microns, such as those available from Murata Manufacturing in Kyoto, Japan.

In some implementations, the diode 110 may have a length in the range of about 200 microns to about 300 microns, a width in the range of about 200 microns to about 300 microns, and a thickness in the range of about 150 microns to about 250 microns. For example, the diode 110 may be implemented using a CDC7630 Schottky diode manufactured by Skyworks Solutions in Woburn, Mass., which has a length of 250 microns, a width of 250 microns, and a thickness of 200 microns. In some implementations, the electrodes 114 and 115 can be disk electrodes having a diameter of about 200 microns, 225 microns, 250 microns, 275 microns, or 300 microns. The coil 106 used to form the inductor can be configured to achieve a desired level of inductance or to achieve a desired resonance frequency with the capacitor 130. In some implementations, the coil 106 may include about 10 turns, about 20 turns, about 35 turns, about 50 turns, about 75 turns, about 100 turns, about 200 turns or about 300 turns. In some implementations, the coil 106 can be 52 AWG or 56 AWG wire, which may be formed from any type of electrically conductive material, such as copper. Table 1 below shows inductance, self-resonant frequency, and DC resistance for various implementations of the coil 106.

TABLE 1

| Coil Type | Inductance (μH) | Self-Resonant Frequency | DC Resistance (Ohms) |
| --- | --- | --- | --- |
| 100-Turn, 52 AWG | 11.5 ± 2.6 | 42.9 ± 5.6 | 8.1 ± 0.4 |
| 100-Turn, 56 AWG | 13.5 ± 0.8 | 37.0 ± 0.5 | 19.7 ± 0.7 |
| 300-Turn, 52 AWG | 122.7 ± 12.7 | 18.5 ± 1.2 | 35.4 ± 0.4 |
| 300-Turn, 56 AWG | 126.7 ± 17.4 | 16.5 ± 1.0 | 58.6 ± 4.1 |

The values shown in Table 1 correspond to measurements taken for various implementations of the coil 106 as shown in the left-most column of Table 1. The coils were formed from insulated copper wire of either 52 AWG or 56 AWG, and were wound around a ferrite core having a diameter of about 2.0 millimeters. The coils had a winding length in the range of about 0.5 millimeters to about 1.0 millimeters. The inductance values were measured using a 1 MHz test frequency.

Figure 2:
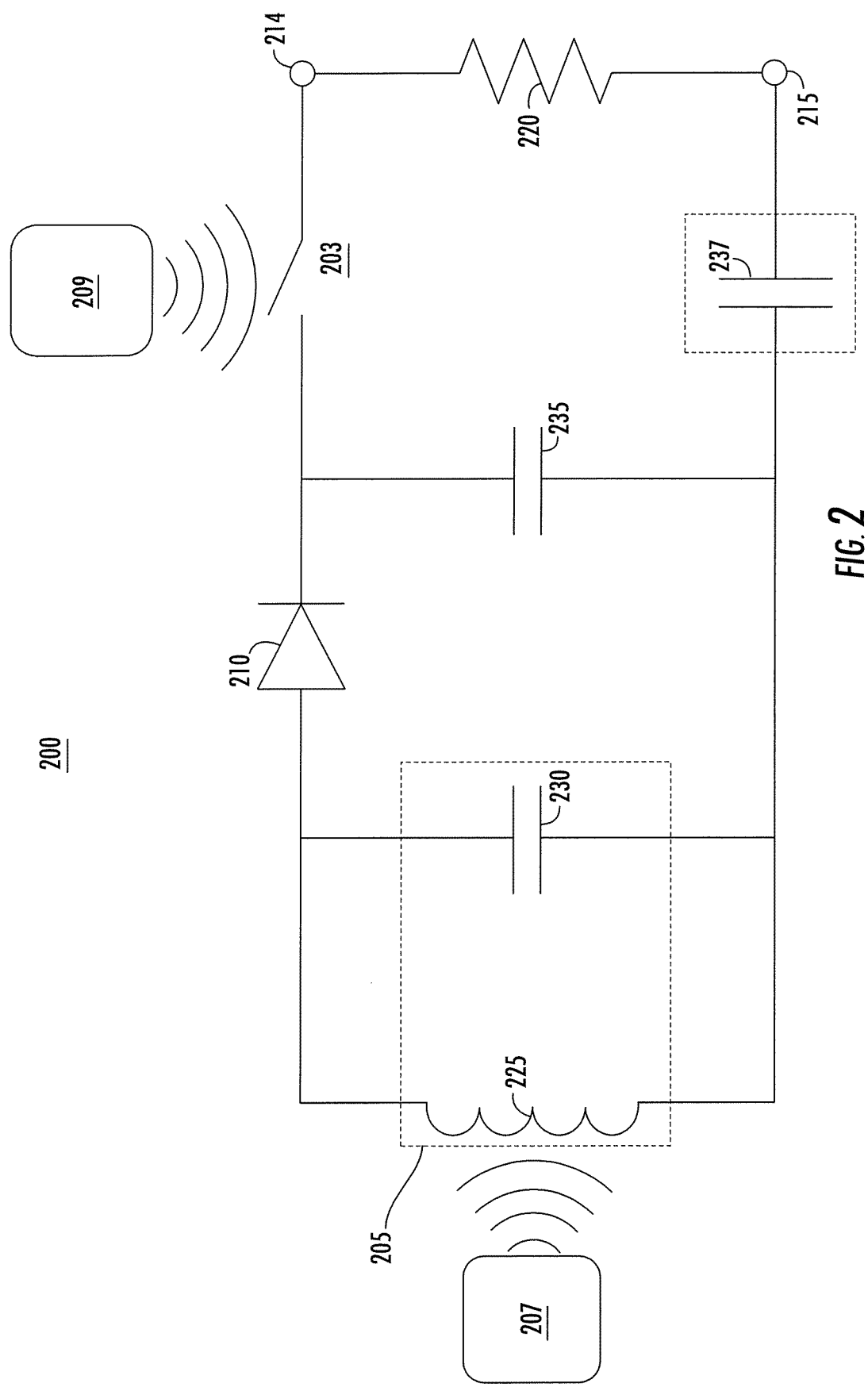
FIG. 2 shows a schematic diagram of another example implantable wireless microstimulator, according to an illustrative implementation described herein.

FIG. 2 shows a schematic diagram of another example implantable wireless microstimulator 200, according to an illustrative implementation. The microstimulator 200 includes many of the features discussed above in connection with the microstimulator 100 shown in FIG. 1A, and like reference numerals refer to like elements. For example, the microstimulator 200 includes an energy harvesting circuit 205, which in this implementation is formed from an inductor 225 in parallel with a capacitor 230. The energy harvesting circuit 205 receives a signal from a power signal generator 207, and generates an electrical signal that is rectified by the diode rectifier 210, which is positioned in series with the energy harvesting circuit 205. In addition, the microstimulator 200 includes a charge storage capacitor 235, a switch 203, and an actuation signal generator 209. The microstimulator 200 may also include a capacitor 237. The broken line surrounding the capacitor 237 indicates that the capacitor 237 is an optional component.

The charge storage capacitor 235 is configured to store electrical charge that exists across the charge storage capacitor 235 in response to the rectified signal produced by the diode rectifier 210. When the switch 203 is open, charge stored by the charge storage capacitor 235 has no path through which to be discharged. As a result, charge will accumulate across the charge storage capacitor 235 while a rectified signal is present at the output of the diode rectifier 210, and the charge storage capacitor 235 will retain the accumulated charge until the switch 203 is closed. It should be noted that, while a charge storage capacitor 235 is shown in FIG. 2, in some implementations, another charge storage element could be substituted. For example, a rechargeable battery could be used as a charge storage element in the microstimulator 200 instead of the charge storage capacitor 235.

When the switch 203 is closed, the charge stored by the charge storage capacitor 235 can be discharged and provide a monophasic neural stimulation pulse through the nervous tissue 220 via the electrodes 214 and 215. Thus, a neural stimulation pulse is only provided to the nervous tissue 220 when the switch 203 is closed. By selectively opening and closing the switch 203, a selected pattern of neural stimulation pulses can be delivered to the nervous tissue 220. In some implementations, the actuation signal generator 209 can be configured to selectively open and close the switch 203 to generate such a pattern of neural stimulation pulses. For example, the switch 203 can be a normally open switch that is configured to close only in response to an applied actuation signal, which may be a wireless signal. The actuation signal generator 209 can transmit an actuation signal that causes the switch 203 to close temporarily, thereby allowing the voltage stored by the charge storage capacitor 203 to be discharged through the nervous tissue 220. One example implementation of the switch 203 is discussed further below in connection with FIG. 3.

In some implementations, the addition of the charge storage capacitor 235 and the switch 203 may counterintuitively allow the size of the microstimulator 200 to be further reduced relative to the size of the microstimulator 100 shown in FIG. 1A, which does not include these components. Incorporating the charge storage capacitor 235 allows for the accumulation of a larger amount of electrical energy in the microstimulator 200, which can be discharged through the tissue 220 in a short pulse by momentarily closing the switch 203. Thus, the microstimulator 200 can be capable of transmitting short pulses at a higher average power than the average power of the neural stimulation signal produced by the microstimulator 100 shown in FIG. 1A. As a result, the components of the microstimulator 200 can be made smaller and the microstimulator 200 can still be capable of delivering neural stimulation pulses of sufficient power, even when taking into account the increased electrical resistance that may occur due to the relatively smaller components.

In some implementations, the switch 203 can be configured to close for a duration of time equal to a desired duration of the neural stimulation pulse. For example, in some implementations, the desired duration of the neural stimulation pulse may be about 0.1 milliseconds, about 0.2 milliseconds, about 0.3 milliseconds, or about 0.4 milliseconds. The neural stimulation pulse may have a charge output (i.e., an integrated current) in the range of about 5 nC to about 15 nC and a voltage in the range of about 0.5 volts to about 1.5 volts. In some implementations, the neural stimulation pulse may have a charge output of about 10 nC and a voltage of about 1 volt.

The microstimulator 200 also can be individually activated independently of other such microstimulators 200 that may also be implanted within the patient. For example, the switch 203 can be configured to respond to an actuation signal that differs from an actuation signal associated with the switch of another implantable microstimulator. Thus, multiple instances of the microstimulator 200 can be implanted in the patient, and each can be activated independently to achieve a desired therapeutic effect. In some implementations, a group of two or more microstimulators 200 may be configured to respond to the same actuation signal, such that the group of microstimulators 200 can be activated simultaneously. Other microstimulators 200 not in the group may be configured to respond to a different actuation signal, so that activation of the microstimulators within the group can be achieved independently of activation of the microstimulators not within the group. An example of a system including multiple instances of the microstimulator 200 that can be individually activated in this manner is described further below in connection with FIG. 4. In some other implementations, multiple instances of the microstimulator 200 may be individually activated by selecting appropriate values for the inductor 225 and the capacitor 230 of the energy harvesting circuit 205 for each instance of the microstimulator 200. An example of such a system is discussed further below in connection with FIG. 5.

In some implementations, the optional capacitor 237 may be added to the system 200 to cause the integrated average current through the stimulation electrodes 214 and 215 to be zero. Zero average DC current can help to preserve the impedance properties of some types of neural electrodes, and also may reduce corrosion, pH changes, and local tissue damage as well.

In some implementations, various components of the microstimulator 200 may be included on a single chip, which can help to reduce the overall size of the microstimulator 200. For example, in some implementations, the diode rectifier 210 and one or both of the capacitors 235 and 237 may be included on a single chip. In general, any two or more of the diode rectifier 210, the inductor 225, the capacitor 230, the capacitor 235, and the capacitor 237 may be included on a single chip.

Figure 3:
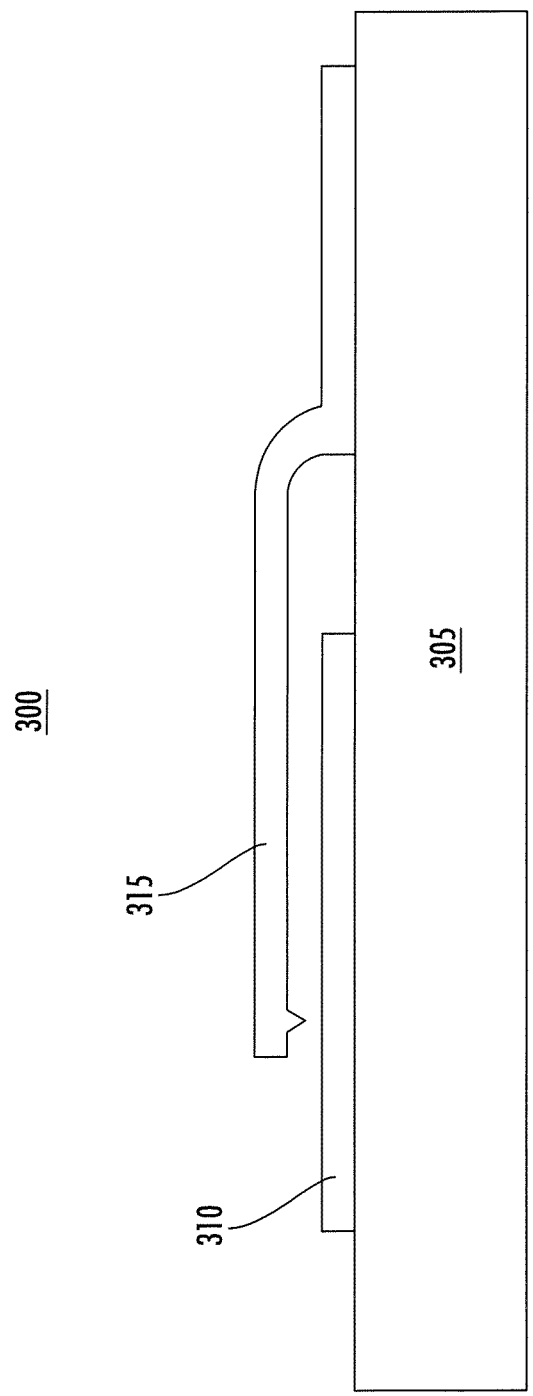
FIG. 3 shows a cross-sectional view of a MEMS reed switch that can be used in the implantable wireless microstimulator of FIG. 2, according to an illustrative implementation described herein.

FIG. 3 shows a cross-sectional view of a microelectromechanical systems (MEMS) reed switch 300 that can be used in the implantable wireless microstimulator of FIG. 2, according to an illustrative implementation. For example, the MEMS reed switch 300 can serve as the switch 203 shown in FIG. 2. The MEMS reed switch 300 is a single-pole, single-throw switch including a substrate 305, a first contact 310, and a second contact 315. The substrate 305 is formed from a non-magnetic material, while the first contact 310 and the second contact 315 are foiined from a magnetic material, such as an iron-nickel alloy. Alternatively, the switch may be electrostatically actuated by the voltage stored on capacitor 235, discharging a pulse whenever the voltage across the switch 203 reaches a level sufficient to actuate the switch.

As shown, the second contact 315 is fixed to the substrate 305 at one end, and the other end of the second contact 315 is suspended above the first contact 310 such that the MEMS reed switch 300 is normally open. When a magnetic field of sufficient amplitude along the long direction of the switch is applied in the vicinity of the MEMS reed switch 300 at a frequency that matches a resonant frequency of the second contact 315, the second contact 315 bends downwards to touch the first contact 310, thereby closing the switch 300. In some implementations, when the MEMS reed switch 300 serves as the switch 203 shown in FIG. 2, the first contact 310 can be electrically connected to the output of the diode rectifier 210 and the second contact can be electrically connected to the electrode 214, as shown in the schematic of FIG. 2. In some implementations, the MEMS reed switch 300 may be configured to close in response to a magnetic field having a frequency that differs from a frequency associated with a different MEMS reed switch 300. This configuration can allow multiple instances of the MEMS reed switch 300 to be actuated independently. In some implementations, the MEMS reed switch 300 can exhibit hysteresis, such that it closes at a higher amplitude magnetic field than is required for it to remain closed. In such implementations, the MEMS reed switch 300 may be operated with a combined DC plus AC magnetic field. The DC field can be selected to be strong enough to hold the MEMS reed switch 300 in a closed position, and the AC field can be tuned to the resonant frequency of selected stimulation nodes.

The MEMS reed switch 300 also can be selected to have a resonant frequency different from the resonant frequency of the signal generated by the power signal generator 207 shown in FIG. 2, so that the MEMS reed switch 300 will not accidentally close in response to the signal generated by the power signal generator 207. As discussed above, the signal generated by the power signal generator 207 may be in the range of about 100 kHz to about 100 MHz. In some implementations, the resonant frequency of the MEMS reed switch 300 may be significantly lower than the frequency of the signal generated by the power signal generator 207. For example, the resonant frequency of the MEMS reed switch 300 may be in the range of about 1 kHz to about 50 kHz. In some implementations, the resonant frequency of the MEMS reed switch 300 may be about 10 kHz. The frequency of the signal generated by the actuation signal generator 209 shown in FIG. 2 can be selected to match the resonant frequency of the MEMS reed switch 300. Thus, in some implementations, the frequency of the signal generated by the actuation signal generator 209 may be in the range of about 1 kHz to about 50 kHz.

It should be noted that the MEMS reed switch 300 is illustrative only, and in some implementations, the switch 203 may be implemented as a different type of switch. For example, the switch 203 may instead be implemented as an electrostatic relay configured to close at a threshold voltage. Thus, when the voltage across the charge storage capacitor 235 shown in FIG. 2 exceeds the threshold voltage associated with the electrostatic relay, the electrostatic relay will close, which allows the charge storage capacitor 235 to be discharged to produce a neural stimulation pulse. After the charge storage capacitor 235 is discharged, the voltage across the charge storage capacitor will again fall below the threshold voltage, and the electrostatic relay will open.

Figure 4:
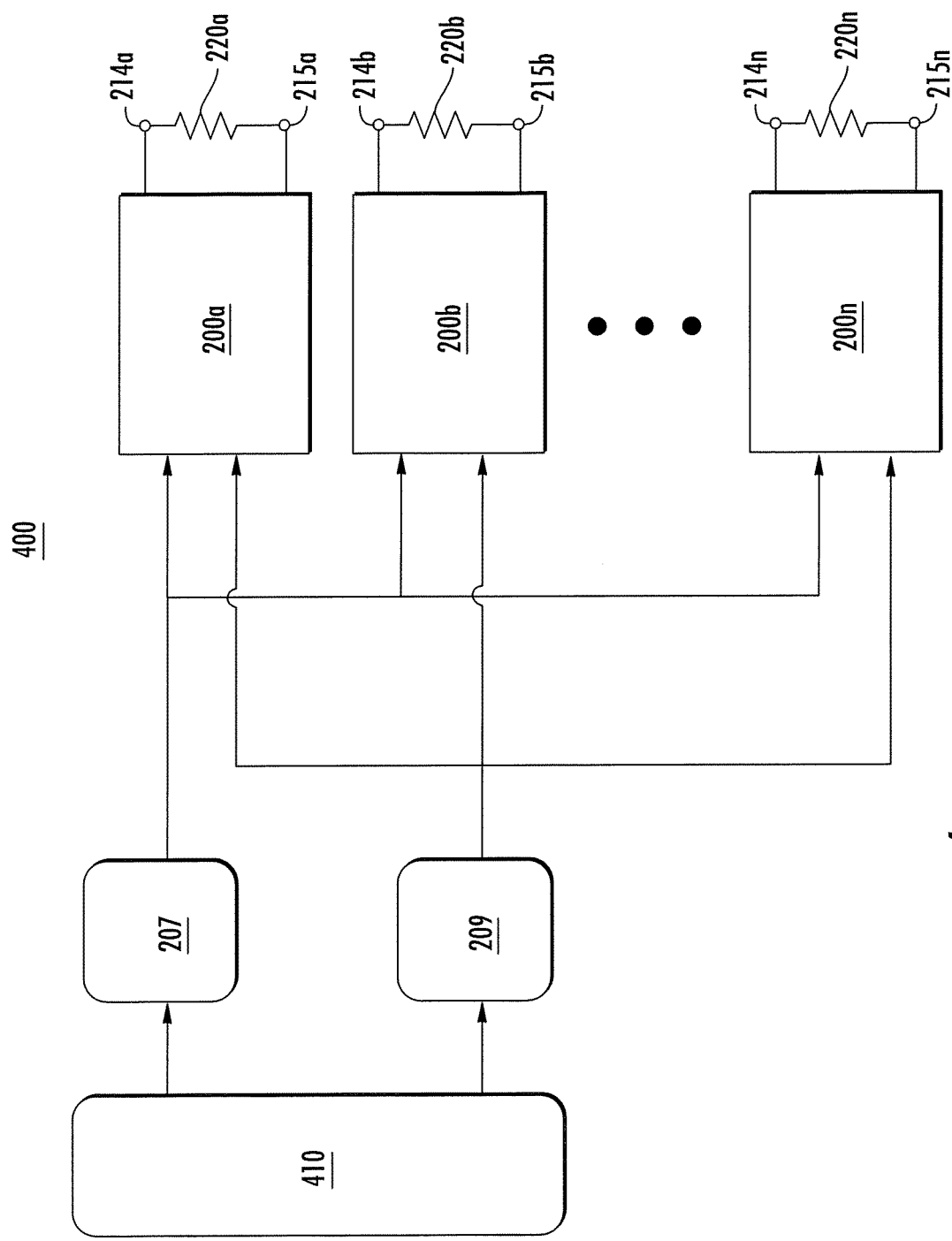
FIG. 4 shows a system including multiple instances of the implantable wireless microstimulator shown in FIG. 2, according to an illustrative implementation described herein.

FIG. 4 shows a system 400 including n implantable wireless microstimulator shown in FIG. 2, according to an illustrative implementation. As shown, the system 400 includes implantable microstimulators 200a-200n (generally referred to as microstimulators 200), each of which is associated with nervous tissue 220a-220n. Nervous tissue 220a-220n can be the same tissue, different tissue, or any combination of subsets of 220a-220n can be the same tissue. A power signal generator 207 and an actuation signal generator 209 communicate with each of the n microstimulators 200. A controller 410 communicates with each of the power signal generator 207 and the actuation signal generator 209.

The system 400 can include any number of microstimulators 200. In some implementations, the system 400 may include tens, hundreds, or thousands of the microstimulators 200, all of which may be implanted into a patient. In some implementations, all of the microstimulators 200 may be implanted near or adjacent to a single target muscle, nerve, brain structure, or other nervous tissue. In some other implementations, a subset of the microstimulators 200 may be implanted near or adjacent to a first targeted portion of muscle, nervous tissue, and another subset of the microstimulators 200 may be implanted near or adjacent to a second targeted portion of nervous tissue. In some implementations, some or all of the microstimulators 200 may be implanted substantially simultaneously. For example, a plurality of microstimulators 200 may be loaded into a syringe, and injected into the patient near or adjacent to the targeted muscle or nervous tissue. In some other implementations, the microstimulators 200 may each be implanted within the patient separately.

The n microstimulators 200 may be used to treat any condition that can benefit from neural stimulation. For example, the microstimulators 200 may be implanted in the brain for cortical or deep-brain stimulation. In some other implementations, the microstimulators 200 may be implanted into peripheral nerves. Stimulation of peripheral nerves can help to treat conditions such as chronic pain, high-blood pressure, or hormonal imbalance. Additionally, using a plurality of microstimulators 200 as shown in FIG. 4, rather than a single microstimulator 200, can help to improve the efficacy of neural stimulation treatment. The microstimulators 200 may be used to stimulate muscles to compensate for damaged or severed nerves, as part of a system to restore motion to a patient.

The n microstimulators 200 can be individually activated to achieve a desired therapeutic effect. For example, it may be desirable to activate only the subset of microstimulators 200 that are positioned near or adjacent to a first targeted portion of nervous tissue without activating other microstimulators 200 that may be implanted elsewhere. As discussed above in connection with FIG. 2, each microstimulator 200 can be activated by closing the switch 203 that allows the charge storage capacitor 235 to be discharged. By appropriately selecting switches 203 that respond to different actuation signals, the system 400 can be configured such that a desired subset of the microstimulators 200 can be activated simultaneously without activating the microstimulators 200 that are not part of the desired subset.

Therefore, all of the microstimulators 200 that are implanted near or adjacent to the first targeted portion of nervous tissue may include switches 203 that respond to an actuation signal having a particular frequency. The controller 410 can cause all of the microstimulators 200 near or adjacent to the first targeted portion of nervous tissue to generate neural stimulation pulses substantially simultaneously by controlling the actuation signal generator 209 to generate an actuation signal with a frequency that matches the frequency associated with switches 203 of the microstimulators 200 that are positioned near or adjacent to the first targeted portion of nervous tissue. Other microstimulators 200 that are not intended to stimulate the first targeted portion of nervous tissue may include switches that actuate in response to an actuation signal having a different frequency.

The above configuration can make use of a simple power signal generator 207, because the triggering of the neural stimulation pulses is managed independently of the energy harvesting. As a result, the power signal generator can emit a constant input signal configured to be converted into an electrical signal by all of the microstimulators 200, even during periods in which it is desired that some of the microstimulators 200 do not deliver a neural stimulation pulse. All of the microstimulators 200 can therefore simultaneously harvest energy from the signal provided by the power signal generator 207. The controller 410 can cause the energy stored by the microstimulators 200 to be selectively discharged to produce neural stimulation pulses by commanding the actuation signal generator 209 to produce actuation signals according to a desired neural stimulation scheme.

In some implementations, a first microstimulator 200a and a second microstimulator 200b are each connected to the same nerve cuff to provide a monophasic neural stimulation pulse via respective electrical interfaces. Microstimulator 200a and microstimulator 200b can be individually activated and are connected such that the polarity of a monophasic neural stimulation pulse is reversed when received from microstimulator 200b as compared to when received from microstimulator 200a. In some implementations, the reversal of polarity can be achieved by reversing the connection of the circuit to electrodes on the nerve cuff (e.g., 214a and 215b are the same electrode and 214b and 215a are the same electrode), or by locating the opposite electrodes in close proximity to each other (e.g., 214a and 215b are located in close proximity to each other and 214b and 215a are located in close proximity to each other in a different location).

Figure 5:
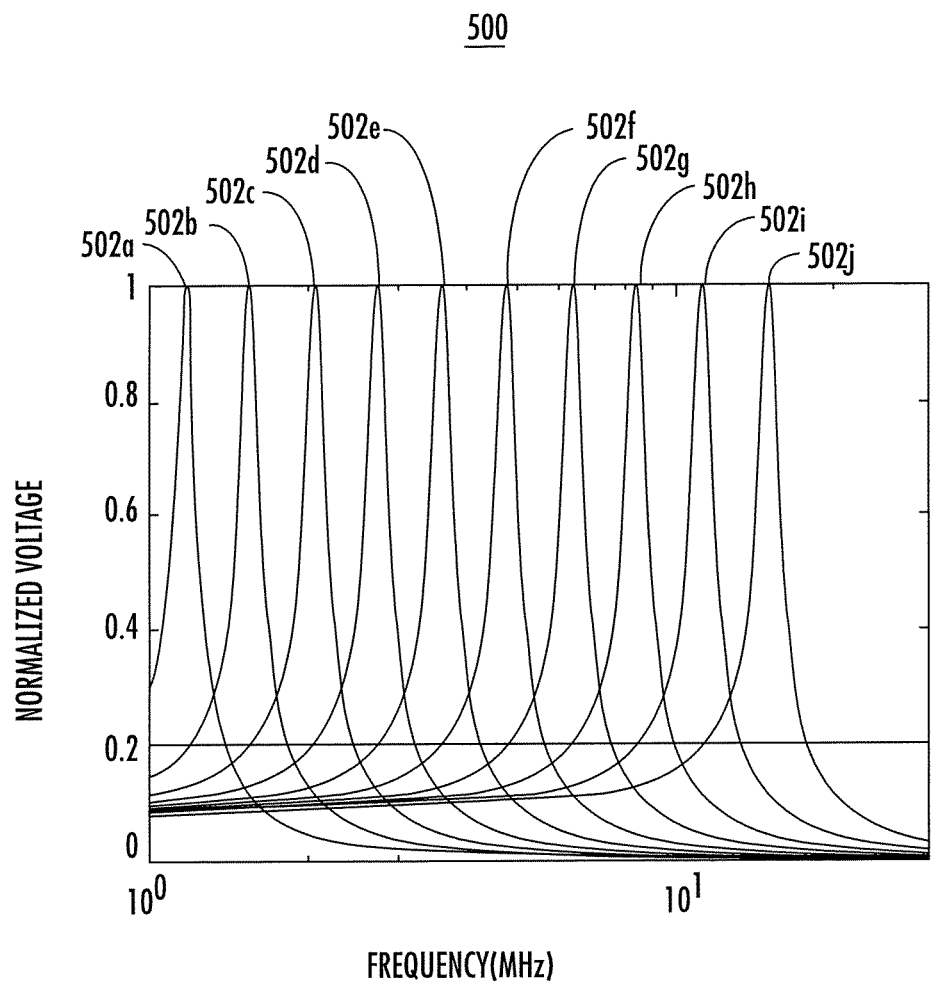
FIG. 5 shows a graph of several example tuning curves each associated with an instance of the implantable wireless microstimulator shown in FIG. 2 over a bandwidth of about 1 MHz to about 15 MHz, according to an illustrative implementation described herein.

FIG. 5 shows a graph 500 of several example tuning curves 502a-502j (generally referred to as tuning curves 502) each associated with an instance of the implantable wireless microstimulator 200 shown in FIG. 2 over a bandwidth of about 1 MHz to about 15 MHz, according to an illustrative implementation. Referring now to FIG. 2, and as discussed above, in some implementations, several instances of the microstimulator 200 may each be individually addressed by selecting appropriate values for the inductor 225 and the capacitor 230 of their respective energy harvesting circuits 205, as well as appropriate input signals from the power signal generator 207. The inductor 225 and the capacitor 230 can be configured to resonate at a particular frequency. When the energy harvesting circuit 205 receives an input signal from the power signal generator 207 that matches the resonant frequency, the energy harvesting circuit 205 can convert the received input signal into a relatively strong electrical signal. An input signal not matching the resonant frequency of the energy harvesting circuit 205 will not cause resonance, and therefore the energy harvesting circuit 205 will convert such a signal into an electrical signal having a substantially lower magnitude that the electrical signal resulting from the conversion of an input signal matching the resonant frequency. In some implementations, the energy harvesting circuit 205 can be configured to produce an electrical signal whose magnitude is negligible in response to receiving an input signal that does not match the resonant frequency of the energy harvesting circuit. Thus, by selecting pairs of inductors 225 and capacitors 230 of the respective energy harvesting circuits 205 of multiple instances of the microstimulator 200 to each resonate at respective unique frequencies, each instance of the microstimulator can be activated individually. The power signal generator 207 can be configured to output a signal having a resonant frequency matching that of the instance of the microstimulator 200 that is intended to be activated. Such a signal will not cause resonance in the other microstimulators 200, and therefore the other microstimulators 200 will not be activated.

Referring now to FIGS. 2 and 5, each of the tuning curves 502 represents the frequency response of an energy harvesting circuit 205 for a particular instance of the microstimulator 200. Each pair of adjacent tuning curves is selected to have an overlap of no more than about 20%, which can help to reduce the likelihood of two energy harvesting circuits 205 resonating in response to the same input signal. As shown, under this constraint, ten unique and substantially non-overlapping tuning curves 502 can be produced over a bandwidth of about 1 MHz to about 15 MHz, which each tuning curve corresponding to a particular configuration for an energy harvesting circuit 205. Thus, up to ten instances of the microstimulator 200 can be individually addressed. The number of individually addressable instances of the microstimulator 200 can be increased, for example, by increasing the bandwidth range or by increasing the allowed maximum overlap between tuning curves. In some implementations, a group of two or more microstimulators 200 may be configured to respond to the same actuation signal, such that the group of microstimulators 200 can be activated simultaneously. Thus, in one example, any of the tuning curves 502 may be associated with the energy harvesting circuit 205 of two or more instances of the microstimulator 200, and each instance of the microstimulator 200 will be activated by an input signal matching the resonant frequency represented by its respective tuning curve.

In some other implementations, as discussed above in connection with FIG. 2, similar principles can be applied to the switches 203 of multiple instances of the microstimulator 200 to achieve individual activation of the microstimulators 200. For example, the switch 203 of each instance of the microstimulator 200 can be configured to resonate at respective unique frequencies, and each instance of the microstimulator 200 can be activated by controlling the actuation signal generator 209 to emit an actuation signal having a frequency matching the resonant frequency of the switch 203 associated with the microstimulator 200 that is to be actuated.

Figure 6:
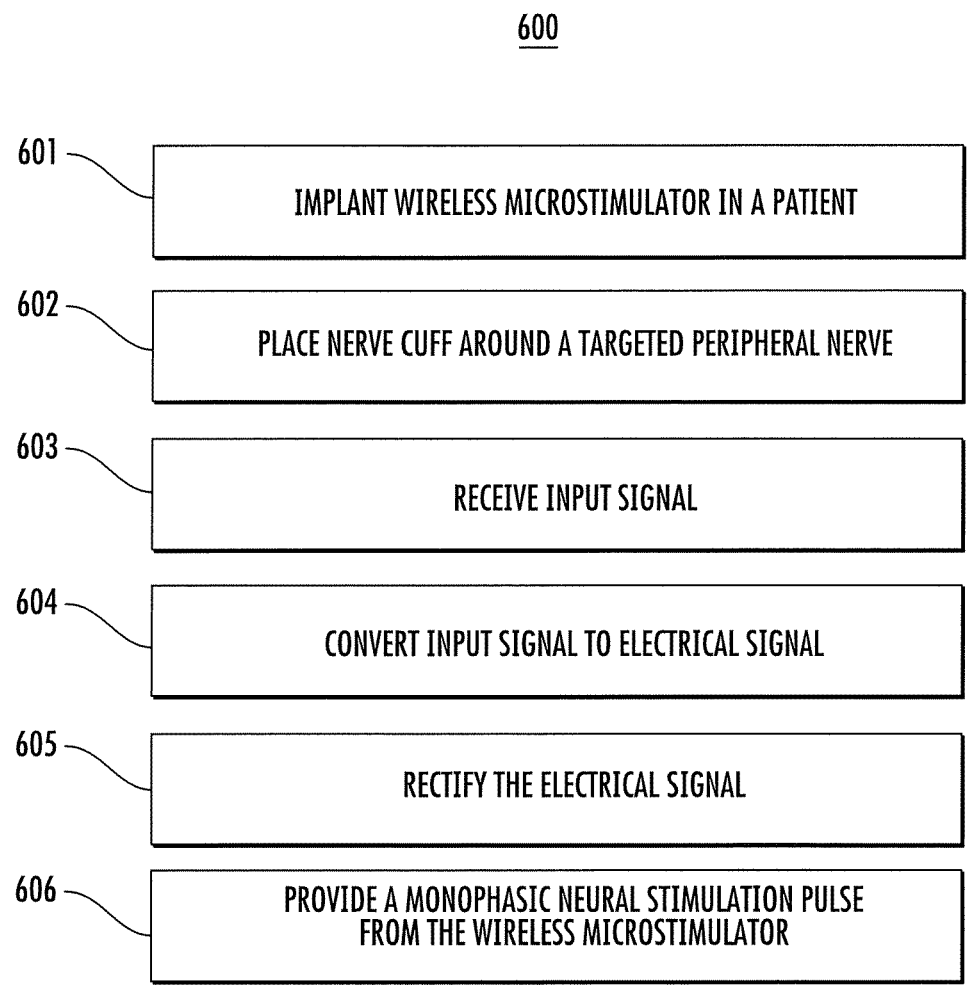
FIG. 6 shows a block diagram of an example method for stimulating a nerve, according to an illustrative implementation described herein.

FIG. 6 shows a block diagram of an example method 600 for stimulating a nerve, according to an illustrative implementation. In brief overview the method 600 includes implanting a wireless microstimulator in a patient (step 601). A nerve cuff with electrode is placed around a nerve so that its electrodes are in direct contact with the nerve (step 602). An input signal is received (step 603). The input signal is converted to an electrical signal (step 604). The electrical signal is rectified (step 605). A monophasic neural stimulation pulse is provided to the nerve through the electrodes (step 606).

In some implementations, the method can be carried out by the implantable neural stimulation microstimulator 100 shown in FIG. 1A. For example, with reference to FIGS. 1A and 6, device 100 can be implanted into a patient connected to a nerve cuff comprising electrodes 114 and 115 (step 601). The nerve cuff can be placed around a targeted peripheral nerve with its electrodes in contact with the nerve (step 602). The energy harvesting circuit 105 can receive an input signal from a power signal generator 107 (step 603). The input signal can be, for example, a magnetic signal whose frequency matches the resonant frequency of the inductor 125 and the capacitor 130 that form the energy harvesting circuit 105. As a result of the resonance, the energy harvesting circuit 105 can convert the input signal received from the power signal generator 107 into an electrical signal (step 604). The diode rectifier 110 can receive the electrical signal from the energy harvesting circuit 205, and can rectify the signal (step 605). This rectified signal can be delivered as a monophasic neural stimulation pulse through the electrodes to a nerve (nervous tissue 120) (step 606).

In some implementations, the method 600 can be carried out by the implantable neural stimulation microstimulator 200 shown in FIG. 2. For example, with reference to FIGS. 2 and 6, device 200 can be implanted into a patient connected to a nerve cuff comprising electrodes 214 and 215 (step 601). The nerve cuff can be placed around a targeted peripheral nerve with its electrodes in contact with the nerve (step 602). The energy harvesting circuit 205 can receive an input signal from a power signal generator 207 (step 603). The input signal can be, for example, a magnetic signal whose frequency matches the resonant frequency of the inductor 225 and the capacitor 230 that form the energy harvesting circuit 205. As a result of the resonance, the energy harvesting circuit 205 can convert the input signal received from the power signal generator 207 into an electrical signal (step 604). The diode rectifier 210 can receive the electrical signal from the energy harvesting circuit 205, and can rectify the signal (step 605). This rectified signal can be provided to the charge storage capacitor 235. The rectified signal causes charge to accumulate across the charge storage capacitor 235. By selectively closing the switch 203, the voltage stored by the charge storage capacitor can be discharged to produce a monophasic neural stimulation pulse through the electrodes to a nerve (nervous tissue 220) (step 606).

Figure 7:
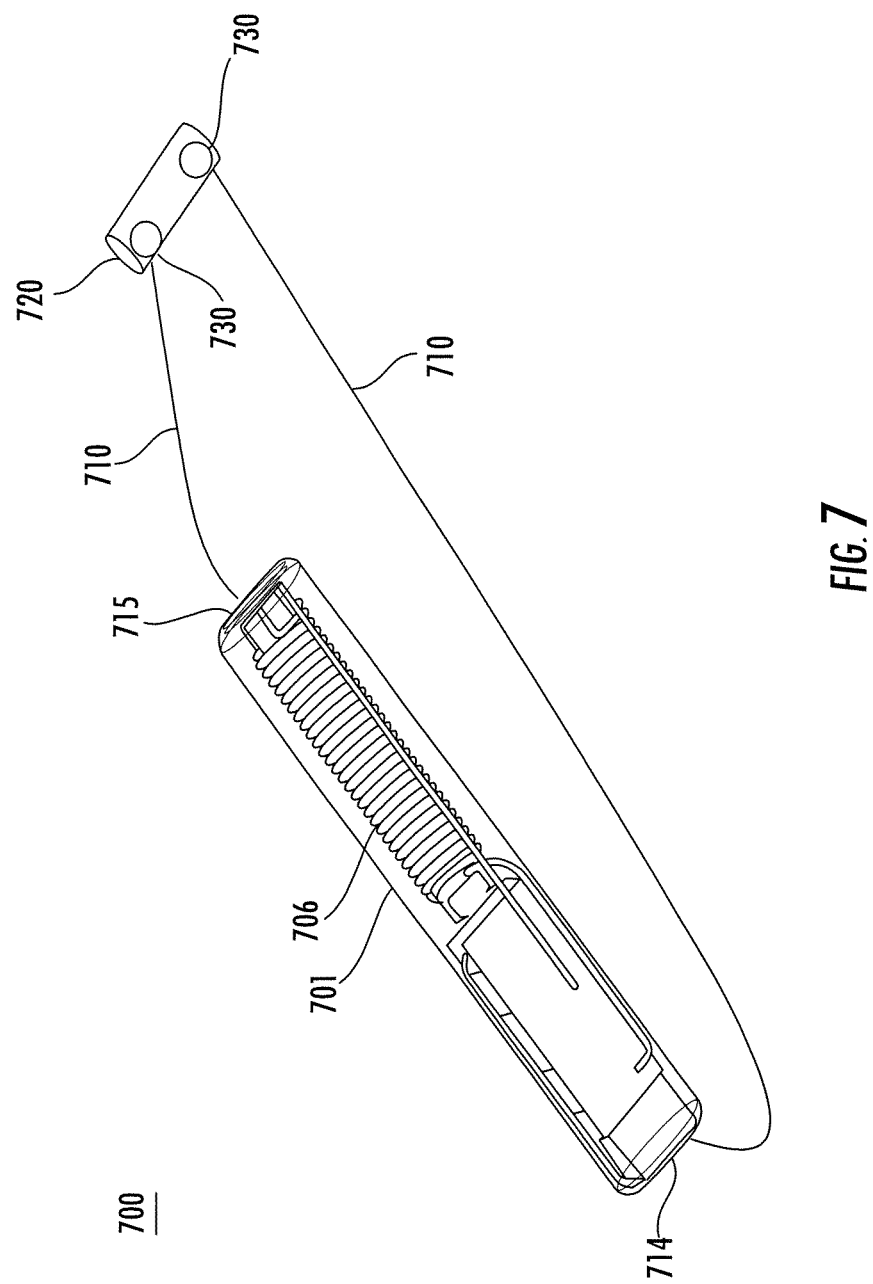
FIG. 7 illustrates an exemplary implantable wireless microstimulator for stimulating peripheral nerves, according to one implementation described herein.

Referring to FIG. 7, an exemplary implantable wireless microstimulator device 700 for peripheral nerves comprises a implantable wireless microstimulator 701, an electrical interface 710, and a nerve cuff 720, all of which components are implantable and adapted for in vivo applications. The electrical interface 710 provides an electrical connection between the implantable wireless microstimulator 701 and electrodes 730 of the nerve cuff 720. In general, more than one implantable wireless microstimulator 701 may connect to a single nerve cuff 720 by means of one or more electrical interfaces 710, in which case each implantable wireless microstimulator 701 may connect to a separate subset of electrodes 730 on the nerve cuff 720.

In some implementations, the electrical interface 710 may connect to the electrodes 714 and 715 of the implantable wireless microstimulator 700, and the connections covered with biocompatible, insulating encapsulant, for example, Parylene, polyurethane, Teflon, silicone or epoxy. In other embodiments, the electrical interface 710 may connect directly to the circuit contained in the implantable microstimulator 701 and be sealed in a biocompatible encapsulating layer that surrounds the microstimulator 701. In these embodiments, the encapsulating layer substantially encloses and seals the components of implantable microstimulator 701 allowing only the electrical interface to be exposed through it.

In some implementations, the electrical interface 710 may comprise two or more electrically conductive wires, which may be insulated and combined in a cable. A greater number of wires may be used to connect a greater number of electrodes 730. The wires may be of stranded or solid construction and composed of stainless steel, platinum, an alloy of platinum and iridium, or another suitable conductor. The insulation may be composed of fluoropolymer or another electrically insulating biocompatible material. While FIG. 7 illustrates the wires of the electrical interface 710 entering opposite ends of the implantable wireless microstimulator 701, they enter the same end in other examples.

In some implementations the nerve cuff 720 has only two electrodes 730 and one is a cathode and one is an anode. In some implementations, more than two electrodes 730 may be arrayed radially or axially along the nerve cuff 720 for purposes of multi-site stimulation or current steering. Embodiments of the nerve cuff 730 are commercially available from Microprobes Incorporated, CorTec, and other manufacturers. The electrical impedance of the nerve cuff 720 when implanted can be chosen as a function of the amount of stimulus current available from the implantable wireless microstimulator 701. In exemplary applications, the preferred nerve cuff 720 is one in which the cuff impedance is less than 10 kΩ at 1 kHz, but greater values of impedance may also be useful. Other properties of the cuff, such as the size, geometry, and number of electrodes, may be optimized for particular applications and are not constrained by any requirement of the implantable wireless microstimulator 701.

The nerve cuff 720 can be implanted by a surgeon so that the electrodes 730 are in direct contact with a targeted peripheral nerve. Stimulus current generated by the implantable wireless microstimulator 701 flows through the electrical interface 710 to the electrodes 730 of the nerve cuff 720. An electrically conductive path through or near or adjacent to the targeted nerve completes the circuit. The nerve cuff 720 is advantageous for stimulating peripheral nerves because its geometry focuses the stimulus current in the vicinity of the cell membrane of the axons in the nerve, where it most effectively stimulates the nerve. A peripheral nerve is any nerve outside the brain and spinal cord, for example the tibial nerve, pudendal nerve, sciatic nerve, superior gluteal nerve, lumbo-sacral trunk, inferior gluteal nerve, common fibular nerve, posterior femoral cutaneous nerve, obturator nerve, common peroneal nerve, plantar nerve, carotid sinus nerve, vagus nerve, or sacral nerves S1, S2, S3, or S4. Stimulation of peripheral nerves can be used to treat such medical disorders as urinary incontinence, overactive bladder, fecal incontinence, urge frequency, non-obstructive urinary retention, high blood pressure, epilepsy, and sexual dysfunction.

Figure 8:
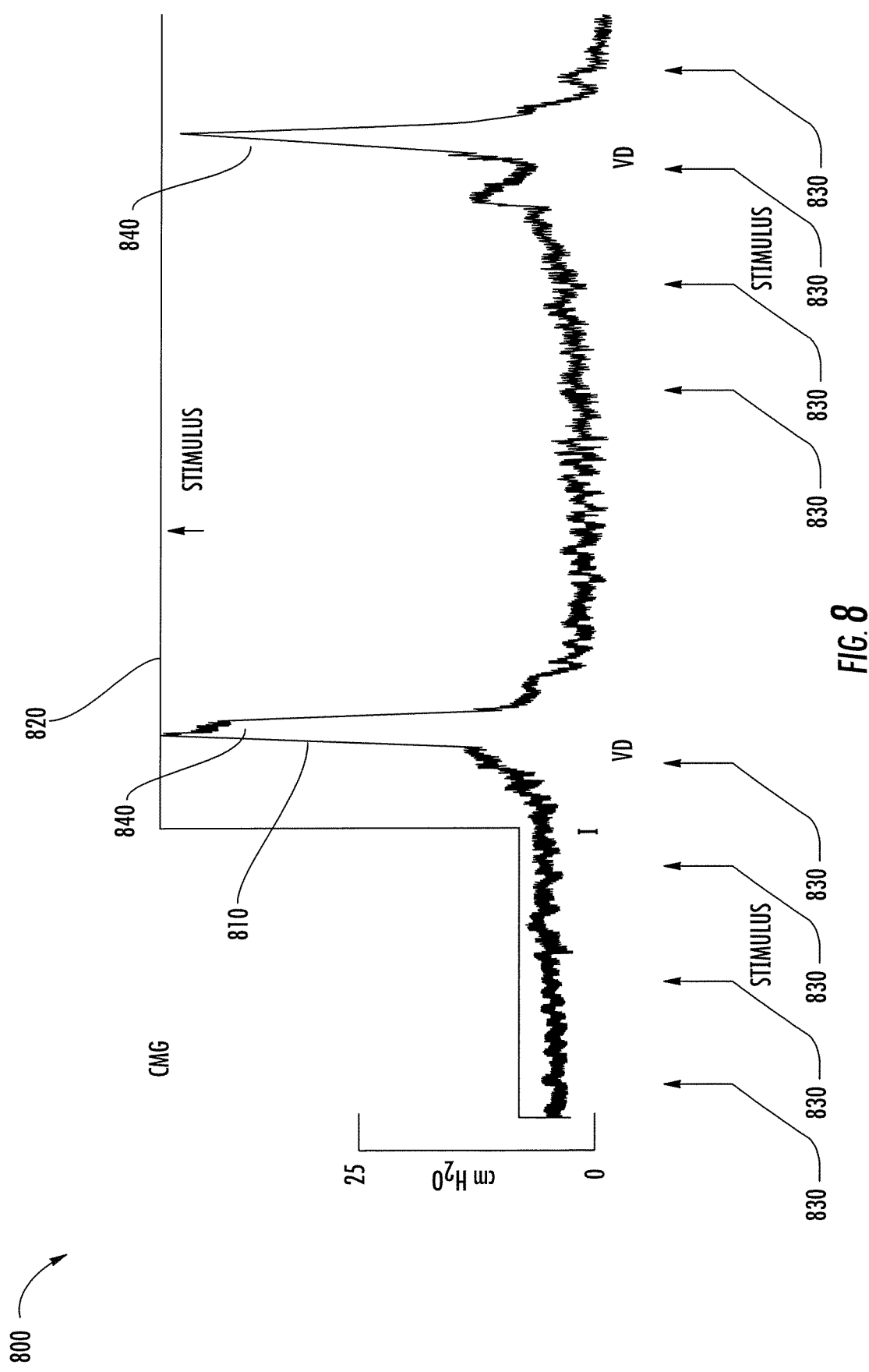
FIG. 8 shows a graph of bladder pressure measured in a Chinchilla rabbit, while a nerve on its pelvic floor was periodically stimulated by an instance of the microstimulator of FIG. 7.

Referring to FIG. 8, an embodiment of the wireless microstimulator device 700 of FIG. 7 was implanted in a Chinchilla rabbit, with the nerve cuff 720 placed around a peripheral nerve on the rabbit's pelvic floor. A particular peripheral nerve was selected because it controls the muscle of the bladder wall. In natural use, nerve impulses transmitted by this nerve cause the bladder to contract and empty of urine. For purposes of quantifying its response during a test of the microstimulator 701, the rabbit was also fitted with a transducer that measured bladder pressure.

The graph 800 shows measurements of bladder pressure 810 as a function of time while the wireless microstimulator 701 was used to create an exemplary stimulus 820. The illustrated stimulus 820 consisted of two sequences of four stimulus pulses 830. Each sequence of stimulus pulses 830 was periodic, with successive pulses separated in time by a uniform interval. Such a sequence mimics the spike trains of nerve impulses that cause the bladder to contract in natural use. The stimulus pulses 830 were generated by an electromagnetic signal having a frequency of 10.7 MHz, modulated at a low frequency to produce the pulse sequences illustrated. The electromagnetic signal was transmitted from outside the rabbit to the implanted wireless microstimulator 701. The signal coupled inductively to the coil 706, which produced a stimulus current that was conducted by an electrical interface 710 to the nerve cuff 720, where it stimulated the nerve. Each peak 840 in bladder pressure 810 documents a contraction of the bladder corresponding to a sequence of stimulus pulses 830. The correlation between bladder contractions and stimulus suggests that the wireless microstimulator 701 successfully stimulated the rabbit's bladder to contract.

The invention claimed is:

1. An implantable wireless microstimulator, comprising:
an energy harvesting circuit configured to receive an input signal and generate an electrical signal based on the received input signal;
a diode rectifier in series with the energy harvesting circuit, the diode rectifier configured to rectify the electrical signal, wherein the energy harvesting circuit and the diode rectifier are encapsulated within a biocompatible electrically insulating material;
an electrical interface exposed through the biocompatible electrically insulating material;
a nerve cuff configured to receive a monophasic neural stimulation pulse through the electrical interface;
a charge storage element configured to store a voltage from an output of the diode rectifier; and
a switch configured to discharge the stored voltage to the electrical interface when the switch is in a closed position, wherein the switch is a normally open switch configured to close in response to a wireless actuation signal; and the switch exhibits hysteresis such that an amplitude of the wireless actuation signal required to close the switch is greater than an amplitude of the wireless actuation signal required to hold the switch in a closed position,
wherein the wireless actuation signal comprises:
a DC component selected to be of sufficient magnitude to hold the switch in a closed position, and
an AC component having a frequency that matches a resonant frequency of the switch, wherein the sum of the amplitudes of the DC component and the AC component is sufficient to close the switch, and
wherein the microstimulator does not include any transistors.

2. The implantable wireless microstimulator of claim 1, wherein the encapsulated combination of energy harvesting circuit and diode rectifier has a volume that is less than 1 cubic millimeter.

3. The implantable wireless microstimulator of claim 1, wherein:
the energy harvesting circuit comprises an inductor in parallel with a capacitor;
the inductor comprises a coil formed from a metal wire wound around a magnetic core; and
the inductor has a diameter that is no greater than 0.6 millimeters and a length that is no greater than 1.2 millimeters.

4. The implantable wireless microstimulator of claim 3, wherein the coil has a wire diameter between 0.009 and 0.026 millimeters and has between 10 and 500 turns.

5. The implantable wireless microstimulator of claim 1, wherein:
the energy harvesting circuit comprises an inductor in parallel with a capacitor;
the inductor has an inductance in the range of 10 nH to 500 µH;

the inductor comprises a coil formed from a metal wound around a ferrite core, the metal being selected from the group consisting of copper, aluminum, silver, gold, and combinations thereof; and the capacitor has a capacitance in the range of 1 pF to 10 nF.

6. The implantable wireless microstimulator of claim 5, wherein the diode rectifier, the inductor, and the capacitor are included within a substantially cylindrical housing and arranged substantially along an axis of the substantially cylindrical housing.

7. The implantable wireless microstimulator of claim 5, wherein the capacitor and the inductor form a circuit having a resonance frequency in the range of 100 kHz to 100 MHz.

8. The implantable wireless microstimulator of claim 1, wherein the biocompatible electrically insulating material is formed from Parylene, silicone, polyurethane, Teflon, epoxy, or a combination thereof.

9. The implantable wireless microstimulator of claim 1, wherein the energy harvesting circuit comprises at least one piezoelectric energy harvester.

10. The implantable wireless microstimulator of claim 1, wherein the nerve cuff comprises an anode and a cathode formed from different materials.

11. The implantable wireless microstimulator of claim 10, wherein:

the cathode is formed from platinum, titanium nitride, or an alloy of platinum and iridium; and the anode is coated with iridium oxide.

12. The implantable wireless microstimulator of claim 1, wherein the switch comprises at least one of a microelectromechanical systems (MEMS) magnetic reed switch or an electrostatically actuated MEMS switch.

13. The implantable wireless microstimulator of claim 1 further comprising an antenna coupled to the energy harvesting circuit, wherein the antenna is configured to:

receive the input signal from a transmitter; and provide the input signal to the energy harvesting circuit.

14. An implantable microstimulation system, comprising:

a plurality of implantable wireless microstimulators, the plurality of implantable wireless microstimulators individually comprising:

an energy harvesting circuit configured to receive an input signal and generate an electrical signal based on the received input signal, a diode rectifier in series with the energy harvesting circuit, the diode rectifier configured to rectify the electrical signal, wherein the energy harvesting circuit and the diode rectifier are encapsulated within a biocompatible electrically insulating material, and an electrical interface exposed through the biocompatible electrically insulating material; and one or more nerve cuffs configured to receive monophasic stimulation pulses through one or more of the electrical interfaces of the plurality of implantable wireless microstimulators, wherein the microstimulators do not include any transistors, and wherein one of the nerve cuffs is connected to the electrical interface of a first implantable wireless microstimulator and is also connected to the electrical interface of a second implantable wireless microstimulator such that the polarity of the monophasic neural stimulation pulse is reversed when received from the second implantable wireless microstimulator as compared to when received from the first implantable wireless microstimulator.

15. The implantable microstimulation system of claim 14, wherein one or more of the plurality of implantable wireless microstimulators individually further comprises:

a charge storage element configured to store a voltage from an output of the diode rectifier; and a switch configured to discharge the stored voltage to the electrical interface when the switch is in a closed position, wherein the switch is a normally open switch configured to close in response to a wireless actuation signal, and wherein the switch exhibits hysteresis, such that an amplitude of the wireless actuation signal required to close the switch is greater than an amplitude of the wireless actuation signal required to hold the switch in a closed position.

16. A method of stimulating a nerve, the method comprising:

implanting the wireless microstimulator of claim 1 in a patient, wherein the nerve cuff further comprises electrodes;

placing the nerve cuff around a targeted peripheral nerve so that the electrodes are in direct contact with the nerve;

receiving an input signal with the energy harvesting circuit of the microstimulator;

converting the input signal into an electrical signal;

rectifying the electrical signal to provide a rectified signal;

providing a monophasic neural stimulation pulse, corresponding to the rectified signal, from the wireless microstimulator to the nerve through the electrodes;

implanting a second wireless microstimulator of claim 1 in a patient; and connecting the nerve cuff to the electrical interface of the first wireless micro stimulator and to the electrical interface of the second wireless microstimulator such that the polarity of the monophasic neural stimulation pulse is reversed when received from the second implantable wireless microstimulator as compared to when received from the first implantable wireless microstimulator.

17. The method of claim 16, wherein the nerve cuff comprises an anode and a cathode formed from different materials.

18. The method of claim 17, wherein the cathode is formed from platinum, titanium nitride, or an alloy of platinum and iridium, and the anode is coated with iridium oxide.

19. The method of claim 16 further comprising:

storing a voltage from an output of the diode rectifier with a charge storage element of the implantable wireless microstimulator.

20. The method of claim 19, wherein the implantable wireless microstimulator further comprises a switch configured to discharge the stored voltage to the electrical interface when the switch is in a closed position.

21. The method of claim 20 further comprising discharging the stored voltage to the electrical interface by switching the switch to the closed position from an open position.

22. The method of claim 16, wherein the implantable wireless microstimulator further comprises an antenna coupled to the energy harvesting circuit, and the method further comprises:

receiving the input signal with the antenna; and providing the input signal from the antenna to the energy harvesting circuit.

* * * * *